United States Patent
Gaurav et al.

(10) Patent No.: US 10,702,169 B2
(45) Date of Patent: Jul. 7, 2020

(54) METHOD AND ELECTRONIC DEVICE FOR CUFF-LESS BLOOD PRESSURE (BP) MEASUREMENT

(71) Applicant: SAMSUNG ELECTRONICS CO., LTD., Suwon-si (KR)

(72) Inventors: Aman Gaurav, Lucknow (IN); Maram Maheedhar, Nandyal (IN); Vijay Narayan Tiwari, Bangalore (IN); Rangavittal Narayanan, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 254 days.

(21) Appl. No.: 15/432,415

(22) Filed: Feb. 14, 2017

(65) Prior Publication Data
US 2017/0238818 A1 Aug. 24, 2017

(30) Foreign Application Priority Data

Feb. 18, 2016 (IN) .............................. 201641005684
Dec. 13, 2016 (IN) .............................. 201641005684

(51) Int. Cl.
*A61B 5/021* (2006.01)
*A61B 5/00* (2006.01)
(Continued)

(52) U.S. Cl.
CPC ........ *A61B 5/02125* (2013.01); *A61B 5/7264* (2013.01); *A61B 5/0261* (2013.01); *A61B 5/0295* (2013.01); *A61B 5/02405* (2013.01); *A61B 5/02416* (2013.01); *A61B 5/486* (2013.01)

(58) Field of Classification Search
CPC ............ A61B 5/02125; A61B 5/02438; A61B 5/02405; A61B 5/02416; A61B 5/021; A61B 5/0205
See application file for complete search history.

(56) References Cited

U.S. PATENT DOCUMENTS 4,754,406 A * 6/1988 Miyawaki .............. A61B 5/022
600/493
2009/0326386 A1 12/2009 Sethi et al.
(Continued)

OTHER PUBLICATIONS

Kurylyak, Y., Lamonaca, F., & Grimaldi, D. (May 2013). A Neural Network-based method for continuous blood pressure estimation from a PPG signal. In Instrumentation and Measurement Technology Conference (I2MTC), 2013 IEEE International (pp. 280-283). IEEE.*

(Continued)

*Primary Examiner* — Jonathan Cwern
(74) *Attorney, Agent, or Firm* — Sughrue Mion, PLLC

(57) ABSTRACT

A method and an electronic device for measuring blood pressure are provided. The method includes illuminating, by a PPG sensor included in the electronic device, skin of a user and measuring a PPG signal based on an illumination absorption by the skin. Further, the method also includes extracting, by the electronic device, a plurality of parameters from the PPG signal, wherein the parameters may comprise PPG features, Heart Rate Variability (HRV) features, Acceleration Plethysmograph (APG) features, and non-linear features. The method also includes estimating, by the electronic device, the BP based on the extracted plurality of parameters.

18 Claims, 11 Drawing Sheets

(51) Int. Cl.
*A61B 5/026* (2006.01)
*A61B 5/0295* (2006.01)
*A61B 5/024* (2006.01)

(56) References Cited

U.S. PATENT DOCUMENTS

| | | |
|---|---|---|
| 2010/0274144 A1 | 10/2010 | Hu et al. |
| 2011/0288421 A1 | 11/2011 | Banet et al. |
| 2012/0029363 A1 | 2/2012 | Lund |
| 2014/0257049 A1 | 9/2014 | Soundarapandian et al. |
| 2014/0329214 A1 | 11/2014 | Bitoun |
| 2015/0073239 A1 | 3/2015 | Pei et al. |
| 2016/0022224 A1 | 1/2016 | Banet et al. |

OTHER PUBLICATIONS

Krishnan, R., Natarajan, B., & Warren, S. (2010). Two-stage approach for detection and reduction of motion artifacts in photoplethysmographic data. IEEE transactions on biomedical engineering, 57(8), 1867-1876.*

Bolanos, M., Nazeran, H., & Haltiwanger, E. (Aug. 2006). Comparison of heart rate variability signal features derived from electrocardiography and photoplethysmography in healthy individuals. In Engineering in Medicine and Biology Society, 2006. EMBS '06. 28th Annual International Conference of the IEEE (pp. 428.*

Hassan, M. K. B. A., Mashor, M. Y., Nasir, N. M., & Mohamed, S. (2008). Measuring of systolic blood pressure based on heart rate. In 4th Kuala Lumpur International Conference on Biomedical Engineering 2008 (pp. 595-598). Springer, Berlin, Heidelberg.*

Qawgzeh et al., "Photoplethysmogram second derivative review: Analysis and applications"., vol. 10(21), Nov. 15, 2015, Academic Journals, pp. 633-639, (7 pages total).

Communication dated Jun. 27, 2018, issued by the European Patent Office in counterpart European Application No. 17753401.3.

Usman et al.; "Second Derivative of Photoplethysmogram in Estimating Vascular Aging among Diabetic Patients"; 2009 International Conference for Technical Postgraduates (TECHPOS); Dec. 2009; 5 pages total.

International Search Report dated Apr. 25, 2017 issued by the International Searching Authority in counterpart International Patent Application No. PCT/KR2017/001230 (PCT/ISA/210).

Communication dated Jan. 7, 2020, issued by the Indian Patent Office in counterpart Indian Application No. 201641005684.

* cited by examiner

METHOD AND ELECTRONIC DEVICE FOR CUFF-LESS BLOOD PRESSURE (BP) MEASUREMENT

CROSS-REFERENCE TO RELATED APPLICATIONS

The present application claims priority from Provisional Indian Application No. 201641005684 filed on Feb. 18, 2016, and Non-Provisional Indian Application No. 201641005684 filed on Dec. 13, 2016. The disclosure of each is hereby incorporated by reference.

BACKGROUND

1. Field

Methods and apparatuses consistent with exemplary embodiments relate to an electronic device using a photoplethysmogram (PPG) sensor for health monitoring such as cardiac health monitoring, renal dysfunctions, etc., of a person, and a method of operating the electronic device, and more particularly, to a method and electronic device for cuff-less Blood Pressure (BP) measurement.

2. Description of Related Art

Hypertension is known to be one of the silent health disorders with a potentially fatal outcome. Symptoms of hypertension are often not detectable until late stages of the disease. Consequently, most individuals are not aware of the disease progression, leading to conditions such as cardiovascular disease, renal dysfunction, etc. Although regular BP checkups at clinics are expected after a certain age, this certain age may not be accurate for most individuals due to the fast paced nature of an urban lifestyle. Also, it has been found that 20% of the patients register at doctor's clinic are for higher BP concerned compared to home settings. Home monitoring of the BP offers an advantage in terms of providing a familiar environment to hypertension patients. Evidence suggests periodic and continuous monitoring of BP can help in early detection of hypertension, thereby reducing mortality. With growing usage of smartphones equipped with PPG sensors, cuff-less BP measurement using a smartphone is feasible.

BP provides a measure of peripheral resistance in blood vessel and is closely related to cardiac function. The upper limit is defined as systolic blood pressure (SBP) while lower limit is defined as diastolic blood pressure (DBP). Sphygmomanometers are the most commonly used devices to accurately measure BP. Although sphygmomanometers are still considered the gold standard for measuring BP, they are mostly confined to clinical set-ups with medical/paramedical staff operating these devices. The method requires the user (i.e., doctor/patient) to inflate the cuff beyond a certain mercury level and auscultate to record the point correctly. This method requires proper training and is not ideal for self-use and continuous monitoring of BP. Further, the devices equipped with cuffs are not portable, and also do not offer on demand measurement capability/continuous monitoring of the BP. This results in a decrease in the reliability of the results obtained by these cuffed devices.

There also exist several methods in which a smartphone based cuff-less BP estimation can operate to check the feasibility of cuff-less BP monitoring through PPG sensor data. The reports obtained based on the PPG sensor data are analyzed and classified into pure PPG signal based, or hybrid approaches comprising both PPG and ECG signals. In another method, smartphones using two PPG sensors located at a known distance are used to estimate pulse wave velocity (PWV) to derive the BP of the user.

In yet another method, the relationship between BP and elasticity of arterial blood vessels (Moens-Kortweg equation) is used to obtain a linear relationship between pulse wave transfer time (PWTT) and BP to correctly estimate the BP. In yet another method, it is possible to compute pulse transit time (PTT) by placing PPG and ECG sensors on finger tips to estimate the BP, and compute the PTT by placing the PPG sensor in an ear lobe and an ECG sensor on the chest The BP estimation using the PTT based approach is more cumbersome, as it requires data from two sensors positioned at different locations on the human body, and this method is also prone to errors because calibration of individual physiological parameters is required. Thus, the aforementioned method(s) is/are dependent on PWV or PTT estimation to estimate the BP.

SUMMARY

One or more exemplary embodiments provide an electronic device for cuff-less Blood Pressure (BP) measurement and a method of operating the device.

One or more exemplary embodiments also provide a method for illuminating, by an electronic device, skin of a user and measuring a PPG signal based on an illumination absorption by the skin. The electronic device also includes a processor connected to the PPG sensor.

One or more exemplary embodiments also provide a method for extracting, by the electronic device, a plurality of parameters from the PPG signal, wherein the parameters may include PPG features, Heart Rate Variability (HRV) features, Acceleration Plethysmograph (APG) features, and non-linear features.

One or more exemplary embodiments also provide a method for estimating, by the electronic device, the BP based on the extracted plurality of parameters.

One or more exemplary embodiments also provide a method for extracting at least one of magnitude data and temporal data available in the PPG signal.

One or more exemplary embodiments also provide a method for extracting APG features from an APG signal derived from the PPG signal.

One or more exemplary embodiments also provide a method for extracting non-linear features based on cardiovascular circulatory system analysis, statistical significance and correlation with the BP values.

One or more exemplary embodiments also provide a method for extracting HRV features by computing a plurality of consecutive peak interval of the PPG signal.

One or more exemplary embodiments also provide a method for receiving, by a recommendation engine, the estimated BP of a user based on a periodic interval, determining, by the recommendation engine, a stressful situation based on the estimated BP, and providing, by the recommendation engine, at least one recommendation to handle the stressful situation.

In accordance with an aspect of an exemplary embodiment, there is provided a method for cuff-less Blood Pressure (BP) measurement, the method including: illuminating skin of a user; measuring a PPG signal based on an illumination absorption by the skin; and extracting, by the electronic device, a plurality of parameters from the PPG signal, wherein the parameters include PPG features, Heart Rate Variability (HRV) features, Acceleration Plethysmograph (APG) features, and non-linear features, and estimating, by the electronic device, the BP based on the extracted plurality of parameters.

The plurality of parameters that are extracted include at least one of magnitude data and temporal data in the PPG signal.

The magnitude features of the PPG signal include at least one of mean value of the window of a PPG signal, a variance value of a PPG signal, a skewness value of the window, and a kurtosis value of the window.

The temporal features of the PPG signal include at least one of a length of a window, a difference of locations of a peak and a first valley with respect to the length of a window, a difference of a peak and a first valley with respect to time, and a difference of a peak and a second valley with respect to time.

The APG features are extracted from an APG signal derived from the PPG signal.

The APG features include at least one of data related to age and arterial information, a location of a dichrotic notch with respect to the length of a window, a location of a dichrotic notch with respect to time, a PPG signal value at a dichrotic notch, a difference of locations of a peak and a dichrotic notch with respect to the length of window, a difference of a peak and a dichrotic notch with respect to time, a difference of locations of a second valley and a dichrotic notch with respect to the length of a window, a location of a diastolic point on PPG signal with respect to time, an APG signal value at the diastolic point in the window, a PPG signal value at the diastolic point in the window, a ratio of APG signal value at the diastolic point to the peak value of APG signal in the window, a ratio of an APG signal value at the dichrotic notch to the peak value of APG signal in the window, a ratio of an APG signal value at the first valley to the peak value of APG signal in the window, an area under the curve of PPG up to the peak of PPG signal, an area under the curve of PPG from the a peak of PPG signal to the diastolic point in the window, and an area under the curve of PPG from diastolic point to the second valley of PPG in the window.

The non-linear features are extracted based on cardiovascular circulatory system analysis, statistical significance, and correlation with the BP values.

The non-linear features include at least one of a ratio of length of a window to a mean value of the window, a ratio of difference of locations of a peak and a first valley with respect to the length of the window to difference of a peak and a second valley with respect to time, a ratio of difference of peak and first valley with respect to time to difference of peak and second valley with respect to time, a ratio of a mean value of the window to the square root of variance value of the window, a ratio of difference of locations of a peak and a dichrotic notch with respect to the length of the window to a difference of the peak and a second valley with respect to time, a ratio of difference of location of second valley and dichrotic notch with respect to the length of window to a difference of peak and second valley with respect to time, a ratio of: a difference of a peak and a dichrotic notch with respect to time to a difference of locations of a pre-dichrotic notch and a dichrotic notch with respect to the length of window, a ratio of difference of locations of a second valley and a dichrotic notch with respect to time to difference of locations of pre-dichrotic notch and dichrotic notch with respect to the length of window.

The HRV features are extracted by computing a plurality of consecutive peak interval of the PPG signal.

The HRV features include at least one of a root mean square of successive difference (RMSSD), a number of pairs of successive RR intervals (i.e., peak to peak intervals of the cardiac cycle) that differ by 50 ms, a number of pairs of successive RR intervals that differ by 20 ms, the mean of the RR interval, a standard deviation of the RR interval, a ratio of standard deviation to mean, a standard deviation of successive differences of RR intervals, a standard deviation of long diagonal axis in Poincare plot, a low frequency power of RR intervals, a high frequency power of RR intervals, and a ratio of low frequency power to high frequency power.

The BP is estimated by determining, via the processor, a diastolic blood pressure (DBP) and a systolic blood pressure (SBP) based on the extracted plurality of parameters.

The DBP is determined, via the processor, based on a combinatorial artificial neural network (ANN) based feedback model and the SBP is derived based on output of the DBP.

Furthermore, the method includes receiving, by a recommendation engine, the estimated BP of a user based on a periodic interval, determining a stressful situation based on the estimated BP, and providing at least one recommendation to handle the stressful situation.

The at least one recommendation is provided based on the plurality of parameters and the estimated BP.

In accordance with an aspect of the another exemplary embodiment, there is provided an electronic device for cuff-less Blood Pressure (BP) measurement, the electronic device including: a photoplethysmogram (PPG) sensor configured to illuminate skin of a user and measure a PPG signal based on the illumination absorption by the skin, and a processor, coupled to the PPG sensor, configured: to extract a plurality of parameters from the PPG signal, wherein the parameters include PPG features, Heart Rate Variability (HRV) features, Acceleration Plethysmograph (APG) features, and non-linear features, and estimate the BP based on the extracted plurality of parameters.

The electronic device may further include a recommendation engine configured to: receive the estimated BP of a user based on a periodic interval, determine a stressful situation based on the estimated BP, and provide at least one recommendation to handle the stressful situation.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

The exemplary embodiments and the various features and advantageous details thereof will be explained more fully with reference to the accompanying drawings. Descriptions of well-known components and processing techniques are omitted so as to not unnecessarily obscure the exemplary embodiments herein. Also, the various exemplary embodiments described herein are not necessarily mutually exclusive, as some exemplary embodiments can be combined with one or more other exemplary embodiments to form new embodiments. The term "or" as used herein, refers to non-exclusive or, unless otherwise indicated. The examples used herein are intended merely to facilitate an understanding of ways in which the exemplary embodiments can be practiced and to further enable those skilled in the art to practice the exemplary embodiments. Accordingly, the examples should not be construed as limiting the scope of the exemplary embodiments.

As is traditional in the field, exemplary embodiments may be described and illustrated in terms of blocks which carry out a described function or functions. These blocks, which may be referred to herein as units or modules or the like, are physically implemented by analog or digital circuits such as logic gates, integrated circuits, microprocessors, microcontrollers, memory circuits, passive electronic components, active electronic components, optical components, hardwired circuits or the like, and may optionally be driven by firmware and/or software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the exemplary embodiments may be physically separated into two or more interacting and discrete blocks without departing from the scope of the invention. Likewise, the blocks of the exemplary embodiments may be physically combined into more complex blocks without departing from the scope of the invention.

Unlike the related art systems and methods (e.g., PTT approach), one or more exemplary embodiments provide a PPG based estimation of accurate DBP and SBP deployable on the electronic device.

Unlike the related art systems and methods, one or more exemplary embodiments estimate the BP based on the PPG features including the HRV features and non-linear features, thus providing reliable and accurate monitoring of the BP.

Unlike the related art systems and methods, one or more exemplary embodiments provide a non-invasive PPG based BP estimation system for continuous monitoring and tracking of the user BP, leading to early detection of hypertensive condition.

Figure 1:
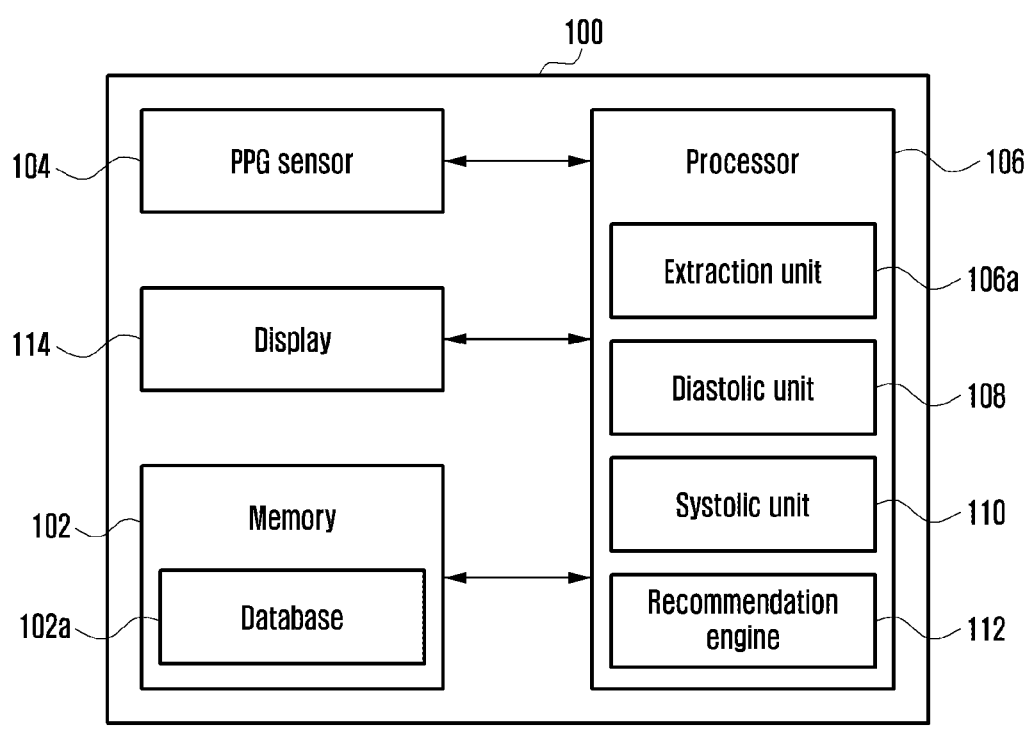
FIG. 1 illustrates a system comprising various units for cuff less Blood Pressure (BP) measurement, according to an exemplary embodiment.

FIG. 1 illustrates a system 100 comprising various units for cuff-less Blood Pressure (BP) measurement, according to an exemplary embodiment.

Referring to FIG. 1, the system 100 includes a memory 102 including a database 102a, a PPG sensor 104, a processor 106, a diastolic unit 108, a systolic unit 110, a recommendation engine 112, and a display unit 114.

In an example, the Cuff-Less Blood Pressure Estimation data set from the database 102a may be employed as the reference database. The database 102a may be derived from physiological data obtained from different organizations database (e.g., Multi-parameter Intelligent Monitoring in Intensive Care (MIMIC-II)). The MIMIC dataset may be collected over, e.g., but not limited to, thousands of people across different age groups at a sampling frequency of e.g., 125 Hz with at least 8-bit accuracy, and extracting the PPG and arterial BP signals of people from this database 102a.

In another embodiment, the database 102a can be externally coupled to the system through wired or wireless connectivity.

The PPG sensor 104 is configured to illuminate skin of a user (i.e., user's skin) and measure a PPG signal based on the illumination absorption by the skin. The PPG sensor 104 may include, for example, at least one periodic light source (e.g., light-emitting diode (LED), or any other periodic light source related thereof), and a photo detector configured to receive the periodic light emitted by the at least one periodic light source reflected from the user's skin.

The PPG sensor 104 can be coupled to the processor 106. In another embodiment, the PPG sensor 104 may be included in a housing with the processor 106 and other circuit/hardware elements.

In another embodiment, the collection of data (e.g., at 100 Hz) in the database 102a using a PPG sensor (for e.g., similar to the PPG sensor 104/different PPG sensor) is interpolated using a cubic spline method to e.g., 125 Hz for testing and deployment of developed solution.

The processor 106 (for example, a hardware unit, an apparatus, a Central Processing Unit (CPU), a Graphics Processing Unit (GPU)) can be configured to receive and process the periodic light received from the PPG sensor 104. The processing includes preprocessing of the data at first instance as discussed below.

Pre-Processing:

In order to extract reliable features (without any PPG & BP artifacts), pre-processing of the data is required. For example, Pan-Tompkins peak detection instructions may be used to extract peaks and valleys of the BP and the PPG signals, and the entire data is divided into windows between consecutive valleys. Windows with inconsistent and erratic BP and HRV may be removed. In order to remove phase lag in collected data, the processed PPG and BP signals are synchronized with each other and used for feature extraction. Further, windows obtained are normalized using min-max scaling in the magnitude range of 0.5 to 1.5 so as to calibrate the PPG sensor 104 with the PPG sensor used in the database 102a.

Feature Extraction:

The processor 106 includes an extraction unit 106a configured to extract the plurality of parameters from the PPG signal, wherein the parameters include the PPG features, the HRV features, the APG features, and non-linear features.

Figure 2:
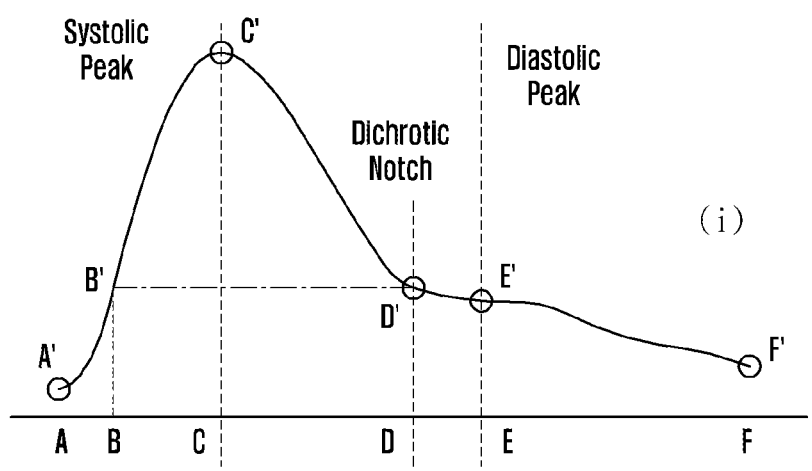
FIG. 2 illustrates a graph of PPG signal from which PPG features are extracted, according to an exemplary embodiment.

Unlike a related art mechanism, the extraction unit 106a, in addition to extracting various features based upon the PPG and APG signal, where the SBP and DBP for each window are calculated by simply determining the peak (for systolic) and the following valley (for diastolic) of the BP waveform, the extraction unit 106a also extracts the HRV based features to improve the BP estimation as shown in FIG. 2, according to an exemplary embodiment.

The recommendation engine 112 can be configured to receive the estimated BP of the user based on a periodic interval. The periodic interval may be preset by the processor 106 and/or by the user. Further, the recommendation engine 112 can be configured to determine the presence of a stressful situation based on the estimated BP. The stressful situation may include, for example, hypertension, due to which the change in the BP may be estimated by the processor 106. Thus, the stressful situation for the user may lead to cardiovascular risks such as heart attack, chest pain (angina), stroke, etc.

Furthermore, the recommendation engine 112 can be configured to provide at least one recommendation to handle the stressful situation. The at least one recommendation may include for example, providing at least one remedy (such as medicine, exercise, etc.) to the user in order to reduce the stressful situation of the user. Additionally or alternatively, the recommendation engine 112 may indicate that the user should relax and/or attempt to remain calm. The at least one recommendation is provided based on the plurality of parameters and the estimated BP.

According to the various embodiments of the present invention, Diastolic unit 108, Systolic unit 110, the recommendation engine 112 can be implemented within the processor 106.

Referring to the FIG. 2, the PPG features extraction is performed on a window of PPG signal based on magnitude data and temporal data available in the PPG signal.

The magnitude features of the PPG signal may include at least one of a mean value of the window of a PPG signal, a variance value of a PPG signal, a skewness value of the window, and a kurtosis value of the window. The temporal features of the PPG signal may include a length of window, a difference of location of peak and first valley with respect to the length of window, a difference of peak and first valley with respect to time, and a difference of peak and second valley with respect to time.

Figure 3A:
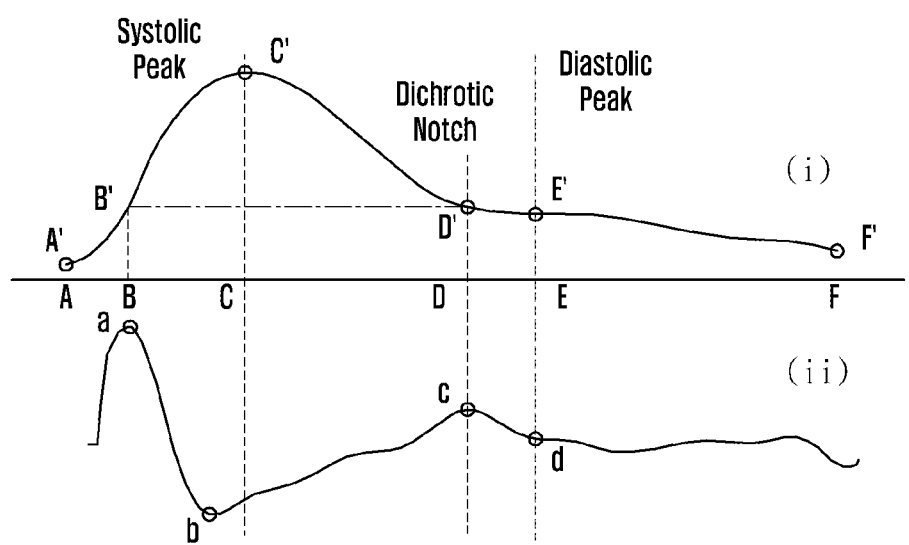
FIG. 3A illustrates a graph of PPG signal of FIG. 2 including corresponding APG signal from which APG features are extracted, according to an exemplary embodiment.

The extraction unit 106a is further configured to extract from the second derivative of a PPG signal an Acceleration Plethysmograph (APG) signal as shown in FIG. 3A, where the window of the PPG signal (i) and the corresponding window of the APG signal (ii) is illustrated according to an exemplary embodiment.

Referring to FIG. 3A, the APG signal may contain information regarding age and other arterial information, and time variation information of APG is also used for feature extraction of an individual which in turn directly affects the BP. The APG signal is used to identify locations (relevant points) of the Dichrotic Notch and Diastolic Peak using derivative analysis as shown in FIG. 43A.

Figure 3B:
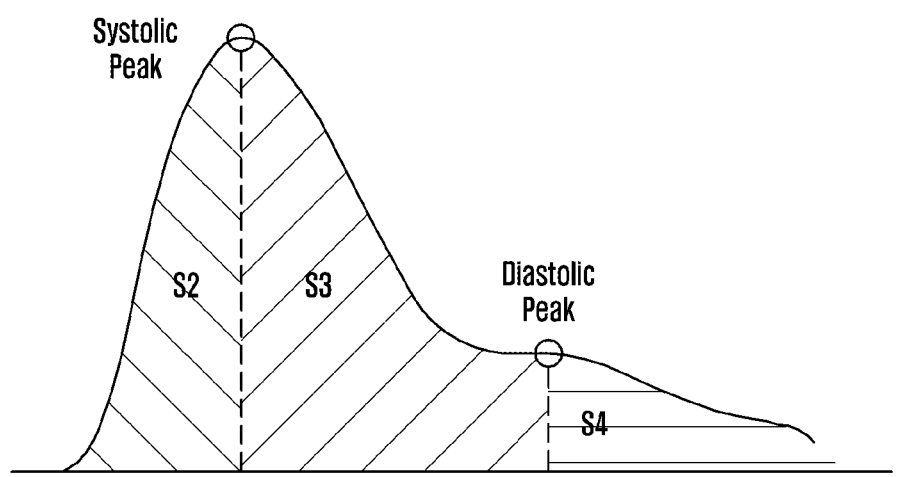
FIG. 3B illustrates a graph of PPG signal used to identify systolic peak and diastolic peak, according to an exemplary embodiment.

Referring to FIGS. 3A and 3B, the APG features are extracted from an APG signal derived from the PPG signal. The APG features include at least one of data related to age and arterial information, a location of a dichrotic notch with respect to the length of the window (AD/AF), a location of a dichrotic notch with respect to time (AD), the PPG signal value at a dichrotic notch (D'), a difference of locations of the peak and the dichrotic notch with respect to the length of window (CD/AF), a difference of the peak and the dichrotic notch with respect to time (CD), a difference of locations of a second valley and a dichrotic notch with respect to the length of window (DF/AF), a location of a diastolic point on the PPG signal with respect to time (AE), an APG signal value at the diastolic point in the window (d), a PPG signal value at the diastolic point in the window (E'), a ratio of APG signal value at the diastolic point to the peak value of the APG signal in the window (d/a), a ratio of an APG signal value at the dichrotic notch to the peak value of the APG signal in the window (c/a), a ratio of the APG signal value at the first valley to the peak value of the APG signal in the window (b/a), an area under the curve of the PPG signal to the peak of the PPG signal (S2), an area under the curve of the PPG signal from the peak of the PPG signal to the diastolic point in the window (S3), an area under the curve of the PPG signal from diastolic point to the second valley of PPG in the window (S4). According to the various exemplary embodiments, features derived from the PPG signal or APG signal can be a linear parameter.

Figure 4:
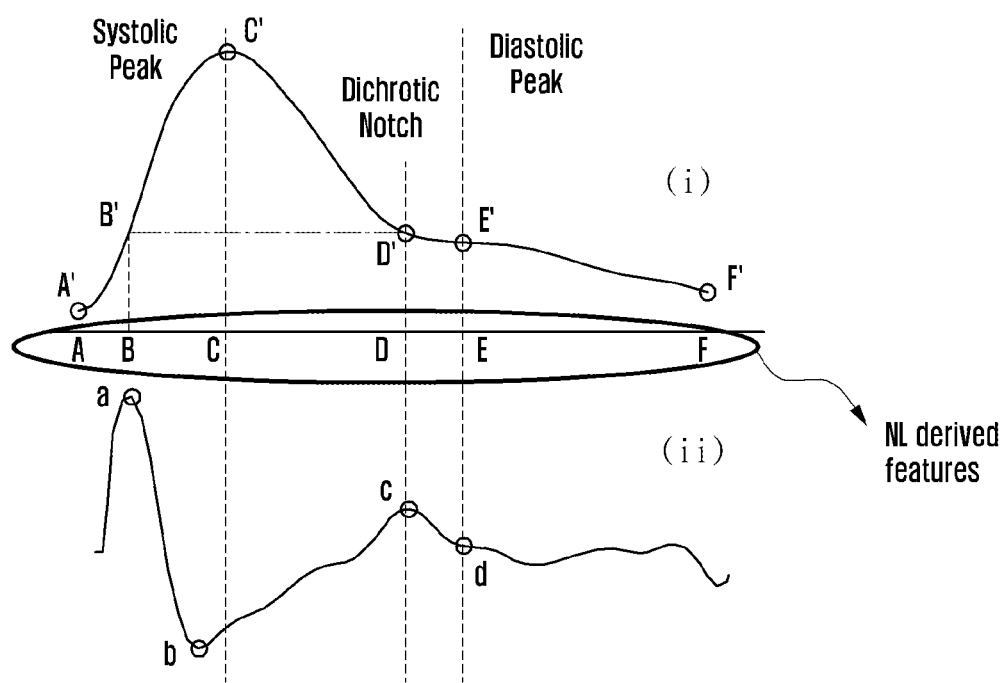
FIG. 4 illustrates a graph of PPG and corresponding APG signal from which non-linear features are extracted, according to an exemplary embodiment.

The extraction unit 106a is further configured to extract the non-linear features based on cardiovascular circulatory system analysis, statistical significance, and correlation with BP values as shown in FIG. 4, according to exemplary embodiments.

Referring to FIG. 4, a novel set of non-linear cardiac cycle time ratio based features are added based on statistical significance and correlation with target BP values, and such features are extracted. Physiological significance of these non-linear feature lies in the fact that time spent in each component of cardiac cycle (atrial contraction, relaxation, ventricular contraction, relaxation) affects the blood volume and the force with which it is pushed into peripheral blood vessels. Peripheral arterial pressure in turn affects the SBP and DBP.

The non-linear features include at least one of: a ratio of a length of the window to a mean value of the window (AF/$\mu$), a ratio of a difference of locations of a peak and a first valley with respect to the length of window, to a difference of a peak and a second valley with respect to time (AC/(AF*CF)), a ratio of a difference of a peak and a first valley with respect to time to a difference of a peak and a second valley with respect to time (AC/CF), a ratio of a mean value of the window to the square of a variance value of the window ($\mu/\sigma2$), a ratio of a difference of location of a peak and a dichrotic notch with respect to the length of the window to a difference of a peak and a second valley with respect to time (CD/(AF*CF)), a ratio of a difference of locations of a second valley and a dichrotic notch with respect to the length of the window to a difference of a peak and a second valley with respect to time (DF/(AF*CF)), a ratio of a difference of a peak and a dichrotic notch with respect to time to a difference of locations of a pre-dichrotic notch and a dichrotic notch with respect to the length of the window ((CD*AF)/BD), a ratio of a difference of locations of a second valley and a dichrotic notch with respect to time to a difference of locations of a pre-dichrotic notch and a dichrotic notch with respect to the length of the window ((DF*AF)/BD).

Referring to FIG. 1, the extraction unit 106a is further configured to extract the HRV features by computing a plurality of consecutive peak intervals of the PPG signal, and the HRV is a result of time spent in each component of cardiac cycle (e.g., if the aortic valve opens prematurely the pulse peak will arrive earlier and if aortic valve closes late, the peak pulse arrival will be delayed.). This will result in higher/lower blood pressure and this variation can potentially be captured by way of the extraction unit 106a. During expiration, the pulmonary and aortic valves close at the same time but during inspiration, the aortic valve closes slightly before the pulmonary. The slower closure of the pulmonary valve is due to lower impedance of the pulmonary vascular tree. Therefore, any change in respiration can affect the HRV which in turn can affect the BP.

According to the study, the HRV data/features may also include implicit information regarding the autonomic nervous system and respiration, both of which have a direct effect on the BP of an individual. The HRV (R-R interval variability) is a measure to evaluate sympathetic and vagal influence on the heart. The HRV is the variation in the time interval between two consecutive heart beats, and it is influenced by a complex interplay between mental thoughts, emotions and external experiences. These features in turn affect the DBP and the SBP which may potentially be captured by including the HRV based features extracted by the extraction unit 106a.

The HRV based features may include, for example, at least one of a root mean square of successive differences (RMSSD), a number of pairs of successive RR intervals that differ by 50 ms, a number of pairs of successive RR intervals that differ by 20 ms, a mean of RR intervals, the standard deviation of RR intervals, a ratio of a standard deviation to a mean, a standard deviation of successive differences of RR intervals, a standard deviation of a long diagonal axis in a Poincare plot, a low frequency power of RR intervals, a high frequency power of RR intervals, and a ratio of low frequency power to high frequency power.

The processor 106 is further configured to process (i.e., post processing) the features extracted by the extraction unit 106a, at a second instance. The features and the BP values are averaged over, e.g., 10 peak windows (from the PPG window signal as illustrated in the FIG. 2) from which the HRV features are calculated. The processor 106 is also configured to process (i.e., post processing) all the features extracted by the extraction unit 106a by assigning a maximum and a minimum threshold for filtering out any erroneous value which may have crept in despite the filtering described. For example, feature values outside a range of $\mu \pm 5\sigma$ (heuristically determined) for a particular feature calculated over the entire dataset may be removed, according to one example.

For example, systolic pressure values<80 mmHg and diastolic pressure values>120 mmHg may be removed. To ensure that blood pressure did not change considerably over this 10 peak window, windows of systolic and diastolic pressures having standard deviation greater than 5 mmHg may be removed. Finally, after combining 10 consecutive windows and post processing, the processor 106 is configured to remove, according to one example, 9% of data and obtain 151,487 (Total peaks/10−erroneous values) blocks of data with plurality of features averaged over 10 windows, along with average target SBP and DBP values.

The processor 106 is further configured to estimate the BP based on the extracted plurality of parameters. The BP is estimated by determining the DBP and the SBP based on the extracted plurality of parameters. The DBP is determined based on a combinatorial artificial neural network (ANN) based feedback model, the SBP is derived based on the output of the DBP as shown in FIG. 5, according to an exemplary embodiment.

Figure 5:
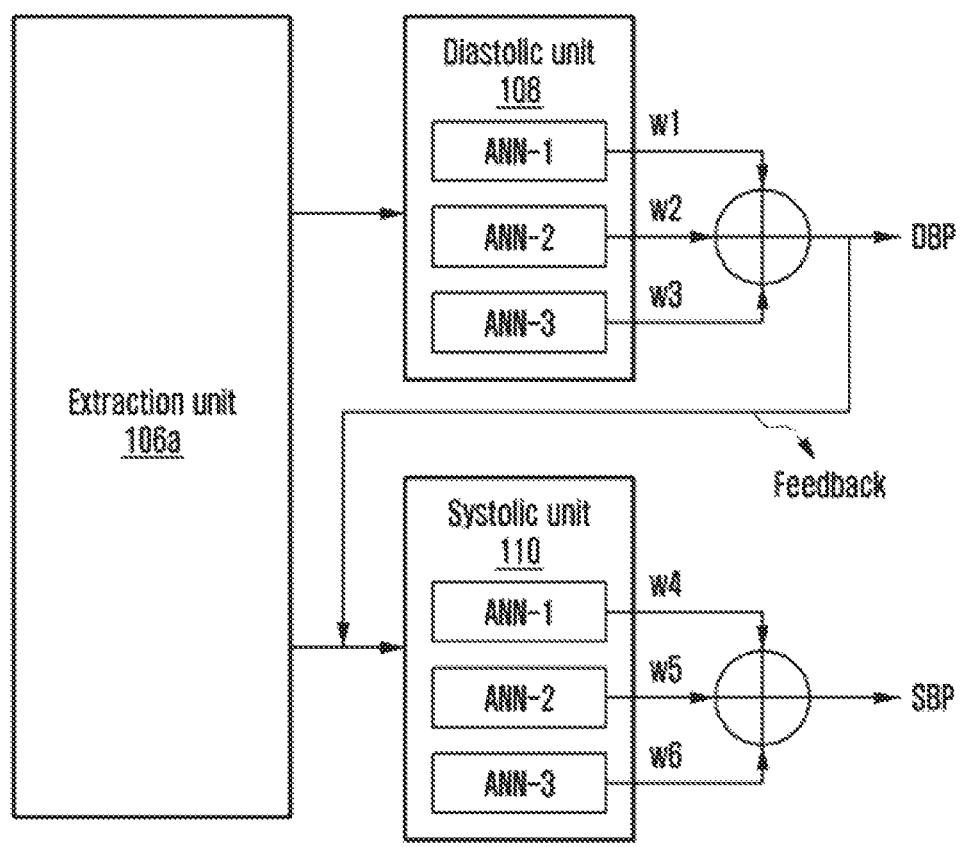
FIG. 5 illustrates an operational model for extracting the DBP and SBP from plurality of parameters extracted, according to an embodiment.

Referring to FIG. 5, a weighted combination of different ANNs (ANN-1, ANN-2, and ANN-3) are used for regression to derive the final DBP and SBP separately. A feedback mechanism (as shown in FIG. 5) is provided from the derived DBP to the systolic model. For example, the diastolic unit 108 is configured to derive the DBP. Further, the processor 106 may be configured to feedback the DBP output derived from the diastolic unit 108 to the systolic unit 110.

The DBP and SBP of a normal person are highly correlated. Hence, the system 100 utilizes the properties of the DBP obtained from the diastolic unit 108 in the systolic unit 110 to obtain the SBP, which in turns improves the accuracy of the system 100 in estimating the BP.

Unlike a related art system, the system 100 provides continuous non-invasive monitoring of the BP with the ability to pick up the BP variations in response to external stimuli.

For example, the processor 106 may be configured to divide the entire dataset (of database 102a) which includes several blocks into two sets randomly in 80:20 ratios. The smaller set is the test set. Validation set in 80:20 ratios randomly three times. Separate models for deriving the SBP (i.e., systolic unit 110) and for the DBP (i.e., diastolic unit 108) are used for training. The larger set is used to train and validate three ANN regression models for each systolic and diastolic pressures using Levenberg-Macquardt instructions, as detailed in FIG. 5. The diastolic unit 108 is trained using plurality of features obtained from the extraction unit 106a. If the dataset includes a large number of individuals, such as, merely by way of example, 3000 individuals with 1,750,000 pulses, then the 4 hidden layers network gives the best representation of the BP variation of the underlying human population without under or over fitting. Hence, separate models with 4 hidden layers and different combination of neurons are used as described in Table 1.

For training the systolic unit 110, an additional feature of DBP (outputted by the diastolic unit 108) along with other features obtained from the extraction unit 106a is utilized. The DBP is a unique feature having a very high correlation of 0.53 with the SBP and hence has potential to improve the accuracy of the SBP. These features (DBP and other features obtained from the extraction unit 106a) are used to train the systolic unit 110 as described in Table 1.

The final output is determined by combining the weighted outputs of the three models. The weights are calculated so as to minimize the standard deviation of the error and are reported in Table 1.

TABLE 1

| Diastolic unit 108 | | Systolic unit 110 | |
|---|---|---|---|
| Hidden layers (Input → Output) | Weights | Hidden layers (Input → Output) | Weights |
| 50, 40, 20, 10 | 0.34 | 50, 25, 35, 20 | 0.31 |
| 50, 20, 30, 20 | 0.21 | 50, 35, 25, 15 | 0.38 |
| 50, 30, 30, 20 | 0.45 | 50, 30, 30, 20 | 0.31 |

The hidden layer network and weights of individual networks are shown in Table 1. The processor 106 is configured to obtain the accuracies of the SBP and the DBP using both existing state of the art (using single PPG sensor in the database 102a) and by way of proposed method for comparison purposes as in Table 2. The results tabulated in Table 2 show a two-fold improvement in accuracy over previous studies by incorporating non-linear, HRV based features and a combination of ANNs with DBP feedback. The accuracies obtained are 0.03±4.72 mmHg for DBP and 0.16±6.85 mmHg for SBP. Further improvement in terms of accuracies can be realized if age and gender information are also provided in the database 102a.

TABLE 2

| Feature sets | Mean Error (mmHg) | | Error Standard Deviation | | Mean Absolute error | |
| --- | --- | --- | --- | --- | --- | --- |
| | Systolic | Diastolic | Systolic | Diastolic | Systolic | Diastolic |
| ONLY PPG + APG | 0.10 | 0.03 | 15.17 | 8.68 | 11.26 | 6.27 |
| PPG + APG + NL + HRV | 0.16 | 0.03 | 6.85 | 4.72 | 4.47 | 321 |

In FIG. 1, the units are shown as a part of the system 100. However, the units (described above) may be part of an electronic device 100 performing functionalities similar or substantially similar as described in conjunction with the FIG. 1 embodiment. The electronic device 100 may be, for example, a mobile device, a wearable device, a laptop computer, a desktop computer, a smart television, a smart display, a notebook computer, a notebook, a tablet or a mobile device such as a mobile phone. Other forms of data processing device are within the scope of the exemplary embodiments discussed herein.

While FIG. 1 illustrates certain units of the system 100, the present inventive concept is not limited thereto. For example, the system 100 may include fewer, or more, units. Additionally, the labels and/or names of the units of the system 100 are provided only for illustrative purpose and do not limit the scope of the exemplary embodiment. For example, one or more units can be combined together to perform the same or substantially similar function(s) in the system 100.

Figure 6:
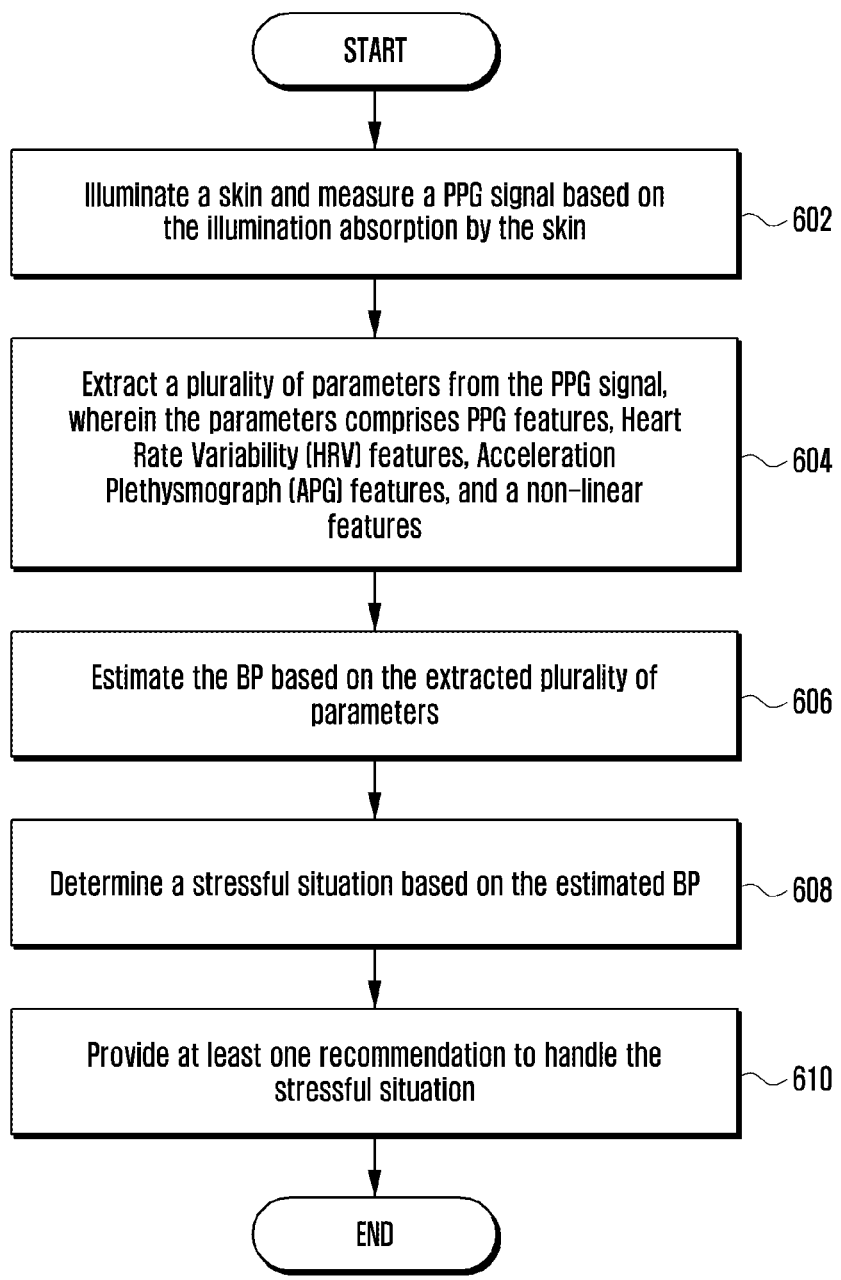
FIG. 6 is a flow diagram illustrating a method for cuff less Blood Pressure (BP) measurement, according to an exemplary embodiment.

FIG. 6 is a flow diagram illustrating a method for the cuff-less BP measurement, according to an exemplary embodiment.

Referring to FIG. 6, in operation 602, the electronic device 100 illuminates skin of a user and measures the PPG signal based on the illumination absorption by the skin. For example, in the electronic device 100, as illustrated in FIG. 1, the PPG sensor 104 is configured to illuminate the skin of the user and measure the PPG signal based on am an illumination absorption by the skin.

In operation 604, the electronic device 100 extracts the plurality of parameters from the PPG signal, wherein the parameters include the PPG features, the HRV features, the APG features, and the non-linear features. For example, in the electronic device 100, as illustrated in the FIG. 1, the processor 106 is configured to extract the plurality of parameters from the PPG signal, wherein the parameters includes the PPG features, the HRV features, the APG features, and the non-linear features.

In operation 606, the electronic device 100 estimates the BP based on the extracted plurality of parameters. For example, in the electronic device 100 as illustrated in the FIG. 1, the processor 106 is configured to extract the plurality of parameters from the PPG signal, wherein the parameters includes the PPG features, the HRV features, the APG features, and the non-linear features.

In operation 608, the electronic device 100 determines that a stressful situation has occurred based on the estimated BP. For example, in the electronic device 100 as illustrated in the FIG. 1, the recommendation engine 112 can be configured to determine that a stressful situation has occurred based on the estimated BP.

In operation 610, the electronic device 100 provides the at least one recommendation to handle the stressful situation. For example, in the electronic device 100 as illustrated in FIG. 1, the recommendation engine 112 can be configured to provide the at least one recommendation to manage the stressful situation.

The various actions, acts, blocks, operations, etc., as illustrated in the FIG. 6 may be performed in the order presented, in a different order, or simultaneously. Further, in some embodiments, some of the actions, acts, blocks, operations, etc., may be omitted, added, modified, skipped, etc.

Figure 7:
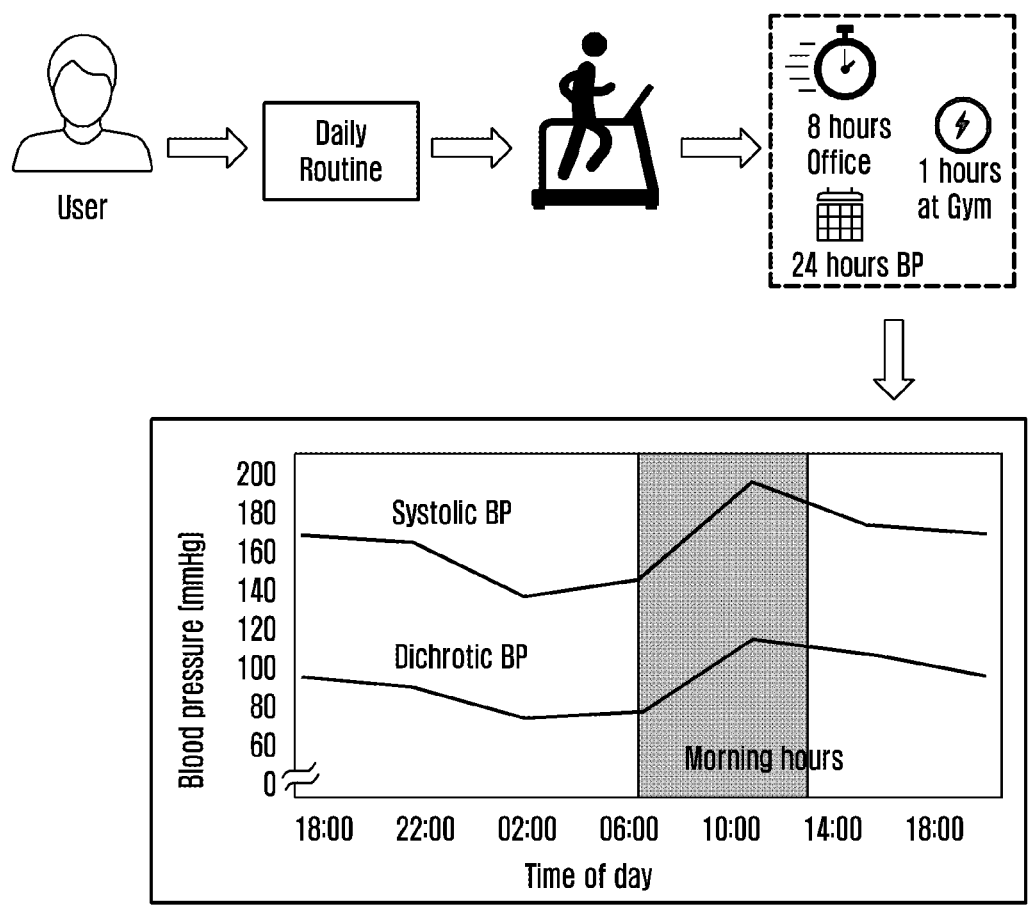
FIG. 7 is an example illustration in which the user can track the BP measurement during the user daily routine, according to an exemplary embodiment.

FIG. 7 is an example illustration in which the user is displayed (by way of the electronic device 100) with BP measurements at different intervals (time) of the day, along with the stressful situation associated thereof, according to an exemplary embodiment.

For example, a user may wish to monitor BP throughout the day, e.g., during intense workouts, at work and even during sleep. Thus, by way of the electronic device 100, the user can accurately monitor the BP and identify a stressful situation during which the variation in the BP level of the user exceeds/drops by certain threshold set by the processor 106. The stressful situation may be, for example, panic situations, hypertension, or any other situation that tends to induce biological stress.

Unlike the related art, the electronic device 100 provides a non-invasive cuff-less PPG based BP estimation system which would help users continuously monitor and track their BP, leading to an overall reduction in cardiovascular complications.

Unlike the related art, the electronic device 100 provides continuous personal monitoring of the BP throughout the day to measure the effect of individual lifestyle related activities including mental state on BP (Systolic & Diastolic).

Unlike the related art, the electronic device 100 provides a solution through which the user can identify the stressful situations during the day which led to sudden rise or fall in BP. Further, the recommendation engine 112 can be configured to provide at least one recommendation to manage such stressful situations and alert the users to avoid such stressful situations (at present or in future).

Figure 8:
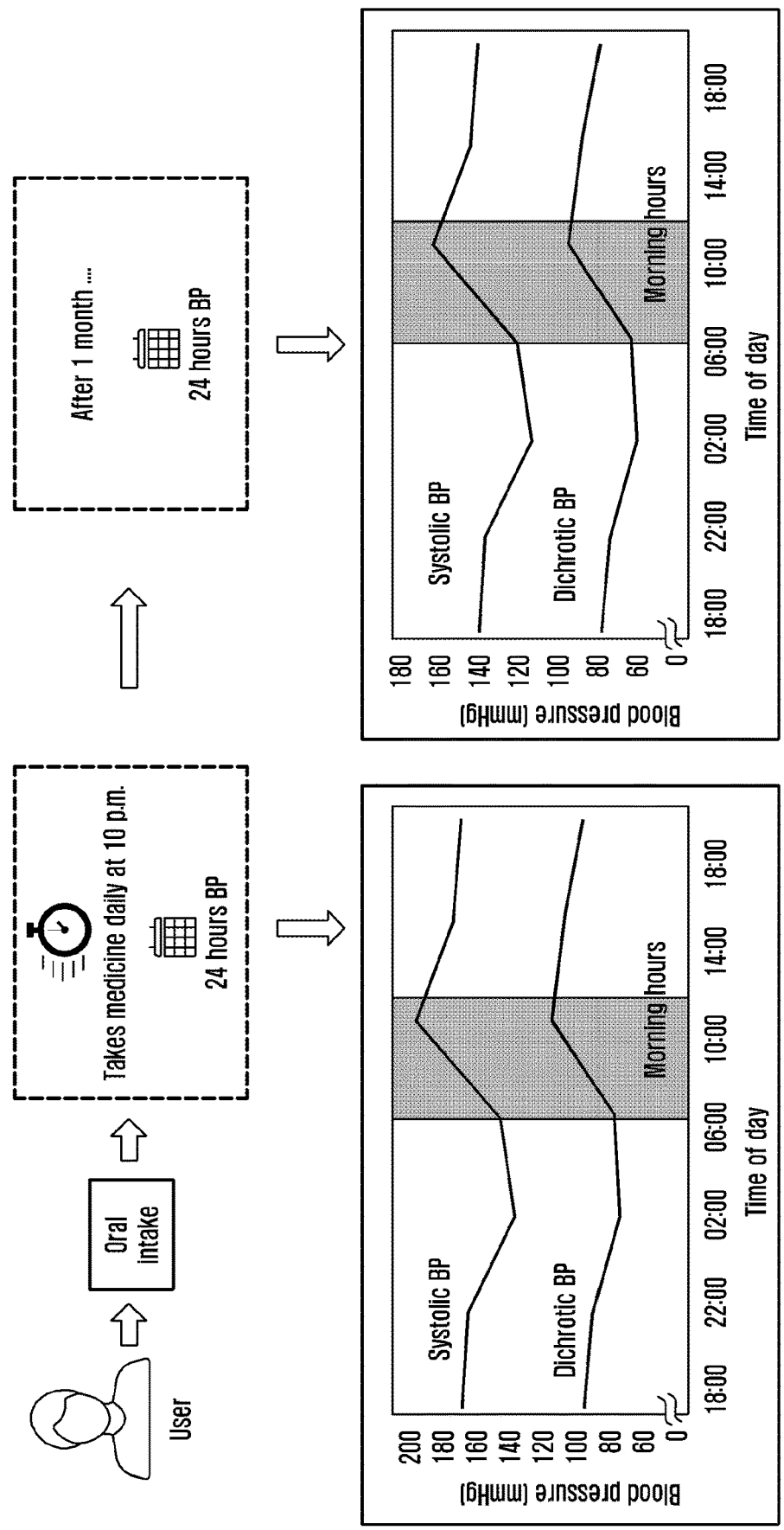
FIG. 8 is an example illustration in which the user is displayed with a BP measurement during medication course for hypertension, according to an exemplary embodiment.

FIG. 8 is an example illustration in which the user is displayed (by way of the display unit 114) with a BP measurement during medication course for hypertension, according to an exemplary embodiment.

The user has been diagnosed with hypertension and takes medication for the same. During the oral intake period, the user consumes the medicine every day at 10 P.M. the user can monitor the BP level after oral intake period by way of the electronic device 100. Thus, the user observes the drop in BP level appreciably during the consumption of the oral intake on time at 10 P.M. The processor 106 may be configured to provide an alert regarding the daily dosage to be taken at 10 P.M, if the BP level of the user does not drop (because he has forgotten to take his/her medicine for the day).

Similarly, after the duration of 1 month, the user observes his/her overall BP level has dropped by around 20 mmHg. The user is now actually in the ideal range of about 120/80 after medication. Thus, because of the alert mechanism provided by the processor 106, the user is now better able to control his/her BP level.

Figure 9:
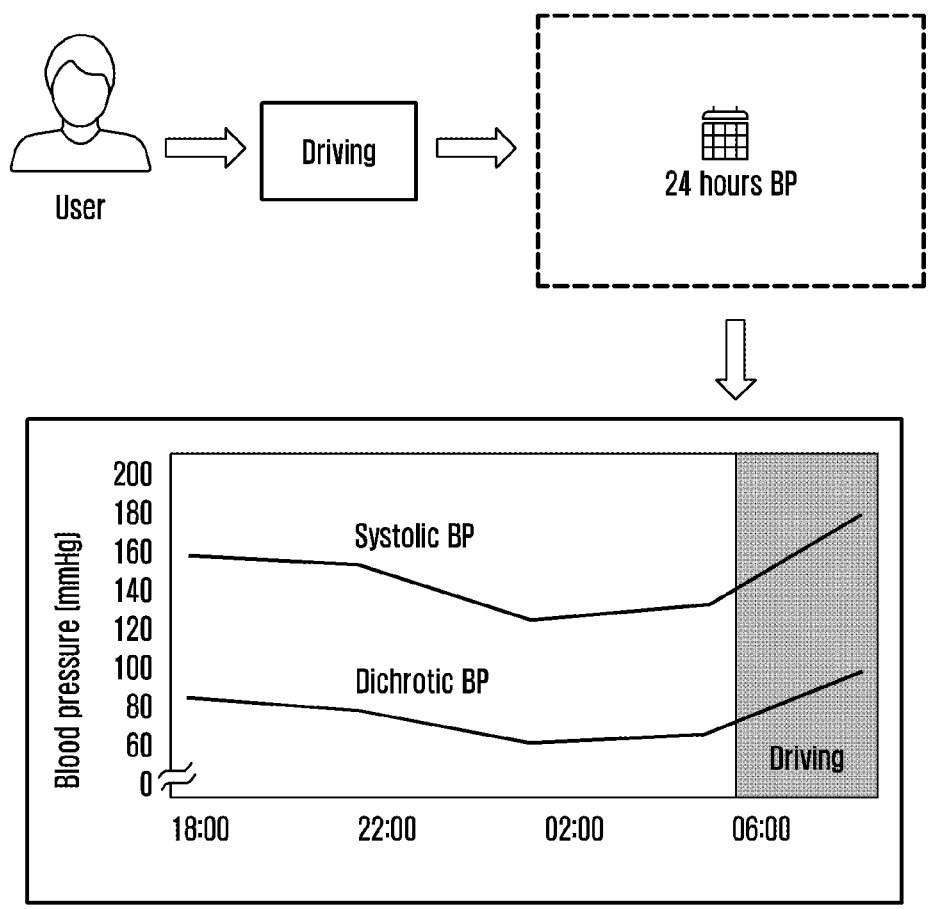
FIG. 9 is an example illustration in which the user is displayed with a BP measurement to identify stressful situations for cardiovascular risk aversion, according to an exemplary embodiment.

FIG. 9 is an example illustration in which the user is displayed (by way of the display unit 114 of the electronic device 100) with the BP measurement during cardiovascular risk aversion, according to an exemplary embodiment.

According to one example, the user (a patient with hypertension) is late in going to the airport to catch a flight to attend a conference. Due to the stress and tension of missing the flight and the conference, his/her BP has risen. The electronic device 100 thus alerts the user to stop doing the intense activity and recommends that he relax or conduct any other aiding mechanism through which the user can reduce his/her BP level.

Figure 10:
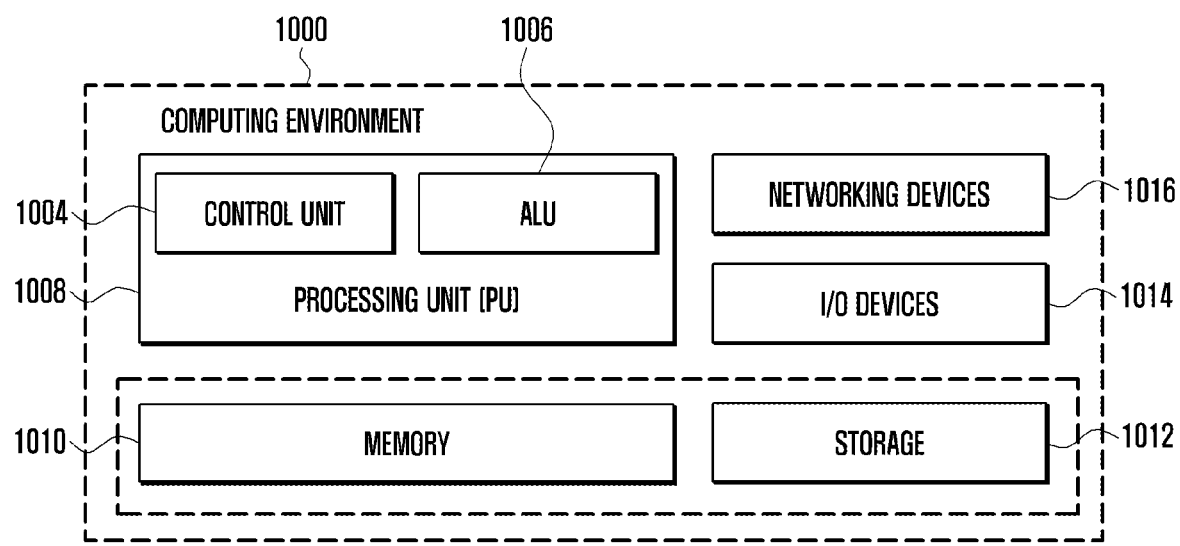
FIG. 10 illustrates a computing environment implementing the method for cuff less Blood Pressure (BP) measurement, according to exemplary embodiments.

FIG. 10 illustrates a computing environment implementing the method for cuff-less BP measurement, according to exemplary embodiments. As depicted in FIG. 10, the computing environment 1000 include at least one processing unit 1008 that is equipped with a control unit 1004 and an Arithmetic Logic Unit (ALU) 1006, a memory 1010, a storage unit 1012, plurality of networking devices 1016 and a plurality of input/output (I/O) devices 1014. The processing unit 1008 is responsible for processing the instructions of the technique. The processing unit 1008 receives commands from the control unit in order to perform its processing. Furthermore, any logical and arithmetic operations involved in the execution of the instructions are computed in conjunction with the ALU 1006.

The overall computing environment 1000 can be composed of multiple homogeneous and/or heterogeneous cores, multiple CPUs of different kinds, special media, and other accelerators. The processing unit 1008 is responsible for processing the instructions of the technique. Furthermore, the plurality of processing units 1008 may be located on a single chip, or over multiple chips.

The instructions and codes required for the implementation of the exemplary embodiments are stored in either the memory unit 1010, the storage 1012, or both. At the time of execution, the instructions may be fetched from the corresponding memory 1010, or storage 1012, and executed by the processing unit 1008.

Various networking devices 1016 or external 110 devices 1014 may be connected to the computing environment to support the implementation through the networking unit and the 110 device unit. For example, the networking device could be a wireless connection circuit that utilizes 4G LTE, 3G, Bluetooth, or Wi-Fi, or a wired connection circuit that utilizes Ethernet or a USB connection. Other types of networking circuitry are feasible.

The exemplary embodiments may be implemented through at least one software program running on at least one hardware device, and performing network management functions to control the elements. The elements shown in FIGS. 1 through 10 include blocks which can be at least one of a hardware device, or a combination of a hardware device and a software module.

The embodiments disclosed herein will be appreciated and understood when considered in conjunction with the preceding description and the accompanying drawings. It should be understood, however, that the preceding descriptions, while indicating exemplary embodiments and numerous specific details thereof, are given by way of illustration and not of limitation. Many changes and modifications may be made within the scope of the exemplary embodiments herein without departing from the spirit thereof, and the embodiments herein include all such modifications.

What is claimed is:

1. An electronic device for measuring Blood Pressure (BP), the electronic device comprising:
a photoplethysmogram (PPG) sensor configured to illuminate skin of a user and measure a PPG signal based on illumination absorption by the skin; and
a processor configured to:
extract a plurality of parameters from the PPG signal, wherein the extracted plurality of parameters are derived from features of the PPG signal,
estimate a diastolic blood pressure (DBP) based on the extracted plurality of parameters, and
estimate a systolic blood pressure (SBP) based on the estimated DBP and the extracted plurality of parameters,
wherein the processor is further configured to:
estimate the DBP by using an artificial neural network (ANN) to output the DBP, and
estimate the SBP, based on the DBP output from the ANN that is fed back into the ANN.

2. The electronic device of claim 1, wherein the plurality of parameters that are extracted comprise at least one of magnitude data and temporal data in the PPG signal.

3. The electronic device of claim 2, wherein the magnitude data of the PPG signal comprises at least one of a mean value of a window of the PPG signal, a variance value of the PPG signal, a skewness value of the window, and a kurtosis value of the window, and
the temporal data of the PPG signal comprises at least one of a length of the window, a difference of locations of a peak and a first valley with respect to the length of the window, a difference of a peak and a first valley with respect to time, and a difference of a peak and a second valley with respect to time.

4. The electronic device of claim 1, wherein the processor is further configured to extract Acceleration Plethysmograph (APG) features from an APG signal, which is a second derivative of the PPG signal, wherein at least one of the APG features is related to age or arterial information.

5. The electronic device of claim 1, wherein the processor is further configured to estimate at least one from among the DBP and the SBP, based on the extracted plurality of parameters related to the PPG signal and non-linear features, and
wherein the non-linear features are extracted based on cardiovascular circulatory system analysis, statistical significance, and correlation with BP values.

6. The electronic device of claim 1, wherein the processor is further configured to estimate the DBP based on a combinatorial artificial neural network (ANN) based feedback model.

7. The electronic device of claim 1, wherein the electronic device further comprises a recommendation engine implemented by the processor, the recommendation engine being configured to:
receive the estimated DBP and the estimated SBP of the user based on a periodic interval;
determine whether a stressful situation has occurred, based on at least one from among the estimated DBP and the estimated SBP; and
provide at least one recommendation to the user to manage the stressful situation.

8. The electronic device of claim 7, wherein the at least one recommendation is provided based on the plurality of parameters and at least one from among the estimated DBP and the estimated SBP.

9. The electronic device of claim 1, wherein the processor is further configured to estimate the DBP and the SBP based on the extracted plurality of parameters and heart rate variability features, and
wherein the heart rate variability features are extracted by computing a plurality of consecutive peak intervals of the PPG signal.

10. A method for measuring Blood Pressure (BP), the method comprising:
illuminating, by a photoplethysmogram (PPG) sensor, skin of a user;
receiving, by the PPG sensor, a PPG signal based on illumination absorption by the skin;
extracting, by a processor, a plurality of parameters from the PPG signal, wherein the extracted plurality of parameters are derived from features of the PPG signal;
estimating a diastolic blood pressure (DBP) based on the extracted plurality of parameters; and
estimating a systolic blood pressure (SBP) based on the estimated DBP and the extracted plurality of parameters,
wherein the estimating the DBP comprises estimating the DBP by using an artificial neural network (ANN) to output the DBP, and
wherein the estimating the SBP comprises estimating the SBP, based on the DBP output from the ANN that is fed back into the ANN.

11. The method of claim 10, wherein the plurality of parameters that are extracted comprise at least one of magnitude data and temporal data in the PPG signal.

12. The method of claim 11, wherein the magnitude data of the PPG signal comprises at least one of a mean value of a window of the PPG signal, a variance value of the PPG signal, a skewness value of the window, and a kurtosis value of the window, and
the temporal data of the PPG signal comprises at least one of a length of the window, a difference of location of a peak and a first valley with respect to the length of the window, a difference of a peak and a first valley with respect to time, and a difference of a peak and a second valley with respect to time.

13. The method of claim 10, further comprising extracting Acceleration Plethysmograph (APG) features from an APG signal, which is a second derivative of the PPG signal, wherein at least one of the APG features is related to age or arterial information.

14. The method of claim 10, further comprising estimating at least one from among the DBP and the SBP based on the extracted plurality of parameters related to the PPG signal and non-linear features, and
wherein the non-linear features are extracted based on cardiovascular circulatory system analysis, statistical significance, and correlation with BP values.

15. The method of claim 10, wherein the method further comprises:
receiving, by a recommendation engine, the estimated DBP and the estimated SBP of the user based on a periodic interval;
determining, by the recommendation engine, whether a stressful situation has occurred based on at least one from among the estimated DBP and the estimated SBP; and
providing, by the recommendation engine, at least one recommendation to the user to manage the stressful situation.

16. The method of claim 10, wherein the estimating the DBP and the estimating the SBP comprise estimating the DBP and the SBP based on the extracted plurality of parameters and heart rate variability features, and
wherein the heart rate variability features are extracted by computing a plurality of consecutive peak intervals of the PPG signal.

17. A device for measuring blood pressure comprising:
a photoplethysmogram (PPG) sensor configured to illuminate skin of a user and measure a PPG signal based on illumination absorption by the skin; and
a processor that receives data from the PPG sensor;
wherein the processor is configured to:
extract magnitude and temporal parameters from the PPG signal;
determine a derivative of the PPG signal;
extract non-linear features from the PPG signal;
extract heart rate variability features from the PPG signal by computing a plurality of consecutive peak intervals of the PPG signal; and
estimate blood pressure based on the magnitude and temporal parameters, the derivative, the non-linear features, and the heart rate variability features,
wherein the magnitude and temporal parameters, the derivative, the non-linear features, and the heart rate variability features are extracted from the PPG signal,
wherein the processor is further configured to:
estimate a diastolic blood pressure (DBP) based on the magnitude and temporal parameters, the derivative, the non-linear features, and the heart rate variability features, and
estimate a systolic blood pressure (SBP) based on the estimated DBP and the magnitude and temporal parameters, the derivative, the non-linear features, and the heart rate variability features,
wherein the processor is further configured to:
estimate the DBP by using an artificial neural network (ANN) to output the DBP, and
estimate the SBP, based on the DBP output from the ANN that is fed back into the ANN.

18. The device according to claim 17, further comprising a recommendation engine implemented by the processor, the recommendation engine being configured to:
receive the estimated blood pressure of the user at periodic intervals;
determine whether a stressful situation has occurred, based on the estimated blood pressure; and
provide at least one recommendation to the user of the device to manage the stressful situation.

* * * * *